(12) United States Patent
Kreszowski et al.

(10) Patent No.: US 9,261,464 B2
(45) Date of Patent: Feb. 16, 2016

(54) APPLYING EDGE-ON PHOTOLUMINESCENCE TO MEASURE BULK IMPURITIES OF SEMICONDUCTOR MATERIALS

(75) Inventors: Doug Kreszowski, Saginaw, MI (US); John W. Hadd, Saginaw, MI (US)

(73) Assignee: Hemlock Semiconductor Corporation, Hemlock, MI (US)

( * ) Notice: Subject to any disclaimer, the term of this patent is extended or adjusted under 35 U.S.C. 154(b) by 297 days.

(21) Appl. No.: 13/701,913

(22) PCT Filed: Jun. 3, 2011

(86) PCT No.: PCT/US2011/039028
§ 371 (c)(1),
(2), (4) Date: Dec. 4, 2012

(87) PCT Pub. No.: WO2011/153410
PCT Pub. Date: Dec. 8, 2011

(65) Prior Publication Data
US 2013/0075627 A1 Mar. 28, 2013

Related U.S. Application Data (60) Provisional application No. 61/351,791, filed on Jun. 4, 2010.

(51) Int. Cl.
*G01N 21/89* (2006.01)
*G01N 21/95* (2006.01)
(Continued)

(52) U.S. Cl.
CPC ............ *G01N 21/9505* (2013.01); *G01J 3/443* (2013.01); *G01N 21/6489* (2013.01); *G01N 21/94* (2013.01); *G01N 21/9501* (2013.01); *G01N 21/9503* (2013.01)

(58) Field of Classification Search
CPC .................................................. G01N 21/6489
USPC ....................................................... 250/459.1
See application file for complete search history.

(56) References Cited

U.S. PATENT DOCUMENTS

| 5,841,532 A | 11/1998 | Yoshida et al. |
|---|---|---|
| 5,987,160 A | 11/1999 | Harlow et al. |

(Continued)

FOREIGN PATENT DOCUMENTS

| CN | 1497291 | 5/2004 |
|---|---|---|
| CN | 101365937 | 2/2009 |

(Continued)

OTHER PUBLICATIONS

P. McL Colley and E C Lightowlers, "Calibration of the photoluminescence technique for measuring B, P and Al concentrations in Si in the range $10^{12}$ to $10^{15}$ cm$^{-3}$ using Fourier transform spectroscopy," *Semicond. Sci. Technol.*, vol. 2, 1987, pp. 157-166.

(Continued)

*Primary Examiner* — David Porta
*Assistant Examiner* — Hugh H Maupin
(74) *Attorney, Agent, or Firm* — Kim E. Choate (57) ABSTRACT

Provided are photoluminescence spectroscopy systems and methods for identifying and quantifying impurities in a semiconductor sample. In some embodiments, the systems and methods comprise a defocused collimated laser beam illuminating a first sample surface, and collection by a collection lens of photoluminescence from a sample edge at the intersection of the first surface with a substantially orthogonal second surface, wherein the first sample surface is oriented from about 0° to 90° with respect to a position parallel to the collection lens.

15 Claims, 9 Drawing Sheets

(51) Int. Cl.
  *G01N 21/64* (2006.01)
  *G01N 21/94* (2006.01)
  *G01J 3/443* (2006.01)

(56) References Cited

U.S. PATENT DOCUMENTS

| | | | |
|---|---|---|---|
| 6,400,454 | B1 | 6/2002 | Noguchi et al. |
| 6,407,395 | B1 | 6/2002 | Perov et al. |
| 2004/0095572 | A1 | 5/2004 | Iwa et al. |
| 2009/0135418 | A1* | 5/2009 | Wolff .......................... 356/318 |
| 2009/0257058 | A1 | 10/2009 | Urano et al. |
| 2010/0264295 | A1* | 10/2010 | Van Dijk et al. .......... 250/201.4 |

FOREIGN PATENT DOCUMENTS

| | | |
|---|---|---|
| JP | H07190922 | 7/1995 |
| JP | 8-068757 | 3/1996 |
| JP | H09229860 | 9/1997 |
| JP | 2003344285 | 12/2003 |
| JP | 2008170344 | 7/2008 |
| JP | 2009512198 | 3/2009 |
| WO | WO2007041758 | 4/2007 |
| WO | WO 2010/015696 A1 | 2/2010 |
| WO | WO2010015696 | 2/2010 |

OTHER PUBLICATIONS

T. Trupke et al., "Very efficient light emission from bulk crystalline silicon," *Applied Physics Letters*, vol. 82, No. 18, May 5, 2003, pp. 2996-2998.

Y. Song et al., "Theoretical analyses and experimental studies on semiconductor disk lasers," *Opt. Quant. Electron.*, 2009, vol. 41, pp. 39-45.

International Search Report, PCT/US2011/039028, dated Sep. 26, 2011, 5 pages.

International Written Opinion, PCT/US2011/039028, dated Sep. 26, 2011, 11 pages.

M. Song et al., "Energy Loss Spectroscopy and Electron Microscopy of Photoluminescent p-type Porous Silicon Treated with NaOH and $NH_3$ Solutions," *Microsc. Microanal.*, vol. 8 (Suppl. 2), 2002, pp. 332-333.

G. Gule et al., "Edge Photoluminescence of Single-Crystal Silicon at Room Temperature," *Semiconductors*, vol. 39, No. 4, Apr. 2005, pp. 406-408.

State Intellectual Property Office of the People's Republic of China, Application No. 201180027579.5, First Office Action, May 28, 2014.

Japan Patent Office, Application No. 2013-513368, Notice of Reasons for Rejection, Nov. 11, 2014.

\* cited by examiner

Prior Art

APPLYING EDGE-ON PHOTOLUMINESCENCE TO MEASURE BULK IMPURITIES OF SEMICONDUCTOR MATERIALS

CROSS REFERENCES TO RELATED APPLICATIONS

This application is a U.S. national stage of International Application No. PCT/US2011/039028, filed Jun. 3, 2011, which claims priority to U.S. Provisional Application No. 61/351,791 filed Jun. 4, 2010, which are incorporated herein in their entirety.

TECHNICAL FIELD

The present invention relates to determining the quality of semiconductor materials using photoluminescence spectroscopy.

BACKGROUND

The electronic structure of a semiconductor material can be investigated by photoluminescence imaging or photoluminescence spectroscopy techniques. In such techniques, a laser is directed onto a semiconductor sample, such as single crystalline silicon. If a photon emitted from the laser has energy greater than the band gap energy of the sample, then it can be absorbed by the semiconductor and excite electrons directly from the full valence band to the empty conduction band, leaving behind electron "holes" in the valence band. Delocalized pairing of free electrons in the conduction band with holes in the valence band gives rise to electron-hole pairs. If electrostatic forces within an electron-hole pair are sufficient to cause binding of the electron to the hole, an exciton is formed. At low temperatures, non-equilibrium electrons, holes, and excitons can stably bind into a plasma that can undergo condensation to form an electron-hole droplet (EHD).

Excited electrons in the conduction band can return to equilibrium by losing their excess energy and recombining with the valence band. This process of electron-hole pair/exciton annihilation can be studied to yield information about a semiconductor sample, including information about impurities that may be contained therein. In one type of recombination event, exciton decay and recombination occurs at a free lattice site (free exciton) and results in the spontaneous emission of a photon having a wavelength corresponding to the energy released. The released photon is observable by photoluminescence analysis, the spectrum of which provides information about the intrinsic semiconductor.

In another type of recombination event, the decaying electron can become loosely bound at an impurity that provides donor or acceptor bands that are within the band gap energy but are distinct from the valence and conduction bands of the intrinsic semiconductor material. The impurity band can absorb the energy associated with the initial decay of the electron from the conduction band to the impurity band and dissipate it as a phonon. Electrostatic forces between the bound electron and a free hole can cause binding of the electron to the hole to form a bound exciton. Decay of the exciton and recombination of the electron with the valence band is associated with emission of a photon that can be observed by photoluminescence analysis, the resulting spectrum providing information characteristic of the impurity. For example, the shape and intensity of the bound exciton peak can be used to determine the impurity density.

At low temperature, photoluminescence spectra show distinct recombination phenomena—recombination of a bound electron in the impurity band with a free hole, giving rise to a bound exciton peak (BE peak), and recombination of a free electron in the intrinsic semiconductor with a free hole, giving rise to a free exciton peak (FE peak). The wavelength of observed photon emissions depends on the type of recombination center within the sample and whether or not phonons are associated with the recombination process. Most peaks of interest are phonon-assisted emissions, wherein intensity at a given wavelength is related to the number of sites within the sample that are responsible for that emission. Because concentration of an electrically active impurity is proportional to the ratio of the intensities of the BE and FE peaks, photoluminescence analysis is a powerful method for the non-destructive analysis of shallow impurities within a sample.

While photoluminescence analysis is a powerful method for analysis of impurities, its accuracy and sensitivity are complicated by peaks associated with the EHD. Exciton density within a sample increases with increasing intensity of the incident laser, and once a critical exciton density is reached, the EHD can form. Recombination events within the EHD give off characteristic luminescence that results in a broad peak underlying and interfering with the BE and FE peaks in the transverse optical (TO) phonon region of the spectrum (8757-8889 $cm^{-1}$/1142-1125 nm). Moreover, because the EHD peak intensifies and shifts to lower energies with increasing excitation intensity, the interference becomes more pronounced with increasing laser power. Thus, it is often difficult to accurately determine the ratio of BE to FE emissions due to interference from the EHD peak, particularly interference between the EHD and BE peaks. Conventional methods of overcoming the difficulties in resolving the BE and FE peaks from the EHD peaks often involve varying excitation energy, such as operating a laser at lower excitation energies, use of extended data collection periods, use of differing laser wavelengths, or a combination thereof. For example, one conventional approach is to run an instrument at low excitation energies in order to minimize the EHD effect. However, this approach reduces the signal-to-noise in the BE and FE emissions, which makes it difficult to effectively measure impurities in high purity semiconductor materials. Another conventional example for measuring semiconductor materials with low levels of impurities and avoiding the EHD is to take longer instrument scans. However, this approach can be a hindrance for efficiently testing large numbers of samples.

In the silicon industry, two principal types of instruments are used for photoluminescence analysis of impurities—dispersive infrared instruments operating under high sample excitation conditions, and Fourier transform instruments operating under low sample excitation conditions. As practiced, both techniques involve "straight-on" collection of emitted photons from silicon samples, wherein the sample is oriented at a position that is parallel to the collection optics. In this orientation, the silicon sample is illuminated by the laser and the emitted photons are collected from the front surface of the sample by a collection lens having a lens focal point at the front surface.

In summary, conventional photoluminescence analysis can be generalized as having four primary steps: (i) excitation of the front surface of a semiconductor sample with a laser at low temperature, said laser operating at either a fixed or variable power to achieve resolution of BE and FE peaks from EHD peaks in resultant spectra; (ii) emission of photons from the sample, said photons being characteristic of BE, FE, and EHD recombination events; (iii) detection of photons emitted from the front surface of the sample by collection optics that are oriented parallel to the sample; and (iv) analysis of the resultant spectra to determine information about the impurities. Such conventional methods and apparatuses are highly sensitive and can typically identify impurity densities of low parts-per-trillion ("ppt") atoms within the crystal lattice. Nevertheless, there remains a need in the art for more sensitive techniques and apparatuses for identifying and quantifying impurities in semiconductor materials.

SUMMARY

This need is met by various embodiments of the present invention, which provide improved methods and apparatuses for identifying and quantifying impurities in semiconductor materials. In some embodiments, the provided methods and apparatuses may be used to identify and quantify sample impurities at lower densities than achievable using conventional methods and apparatuses.

According to various embodiments, provided is a photoluminescence spectroscopy system for identifying and quantifying impurities in a semiconductor sample, comprising: (i) a laser system adapted to provide a defocused collimated laser beam capable of causing an illuminated semiconductor to photoluminesce; (ii) one or more semiconductor samples, each comprising a first surface adapted to be at least partially illuminated by the defocused laser beam, a substantially orthogonal second surface, and an edge at the intersection of the first and second surfaces, the edge adapted to allow collection of photoluminescence emitted therefrom; and (iii) a collection lens having a lens focal point at the edge of a sample positioned for analysis, the lens adapted to collect photoluminescence at said focal point. The provided system is configured such that when a sample is positioned for analysis, its first surface is oriented to be at an angle of deviation of from about 0° to 90° with respect to a position parallel to the collection lens.

According to various embodiments, also provided are photoluminescence spectroscopy methods for identifying and quantifying impurities in a semiconductor sample, comprising: (i) directing a defocused collimated laser beam onto at least a portion of a first surface of a semiconductor sample positioned for analysis, the sample comprising a substantially orthogonal second surface, and an edge at the intersection of the first and second surfaces adapted to allow collection of photoluminescence emitted therefrom, (ii) generating collectable photoluminescence in the sample, (iii) collecting the photoluminescence from the edge of the sample using a collection lens, the lens adapted to collect emitted photoluminescence at a lens focal point on the edge, and (iv) generating data from the collected photoluminescence, the data corresponding to sample impurity identity, sample impurity quantity, or both. In practice of the provided methods, when the sample is positioned for analysis, its first surface is oriented to be at an angle of deviation of from about 0° to 90° with respect to a position parallel to the collection lens.

These and additional features and advantages of the invention will become apparent in the course of the following detailed description. Unless stated otherwise, the features of the described invention can be used separately or together, or in various combinations or subcombinations. Similarly, unless specifically stated otherwise, method steps may be performed in a different order than that which is described herein.

BRIEF DESCRIPTION OF THE DRAWINGS

A more complete appreciation of the invention and the many embodiments thereof will be readily obtained as the same becomes better understood by reference to the following detailed description when considered in connection with the accompanying drawings, wherein.

DETAILED DESCRIPTION

Features and advantages of the invention will now be described with occasional reference to specific embodiments. However, the invention may be embodied in different forms and should not be construed as limited to the embodiments set forth herein. Rather, these embodiments are provided so that this disclosure will be thorough and complete and will fully convey the scope of the invention to those skilled in the art.

Unless otherwise defined, all technical and scientific terms used herein have the same meaning as commonly understood by one of ordinary skill in the art to which the invention belongs. The terminology used in the description herein is for describing particular embodiments only and is not intended to be limiting. As used in the specification and appended claims, the singular forms "a," "an," and "the" are intended to include the plural forms as well, unless the context clearly indicates otherwise.

The terms "impurity" and "impurities," as used herein are intended to mean impurities within a semiconductor crystal lattice that are capable of acting as an electron donor or electron acceptor, and therefore detectable by photoluminescence analysis. Moreover, the terms are intended to encompass unintentional impurities, as well as intentional dopants. In some embodiments, the methods and apparatuses described herein may be used to measure the presence of group III impurities, group V impurities, or combinations thereof in a sample. In some embodiments, the impurities identified and quantified are selected from boron, phosphorus, arsenic, and aluminum.

As used herein, the term "semiconductor" is intended to mean any material having an electrical conductivity that is between that of conductor and an insulator and that is capable of being analyzed by photoluminescence analysis techniques. Examples of such materials include, but are not limited to, silicon, germanium, gallium arsenide, and silicon carbide. In some embodiments, the provided methods and apparatuses may be used to identify and quantify impurities in silicon samples. Such samples may, in some embodiments, be polycrystalline silicon, monocrystalline, doped, undoped, from float-zoned materials, or from Czochralski materials. In some embodiments, the provided methods and apparatuses may be used for identifying and quantifying impurities in epitaxial layers of a silicon sample.

In various embodiments, provided are improved methods and apparatuses for identifying and quantifying impurities in semiconductor materials. In some embodiments, such methods and apparatuses have particular usefulness in identifying and quantifying impurities at lower densities than achievable using conventional methods and apparatuses, such as at densities as low as from about 0.5 ppt to about 1.5 ppt. Thus, in some embodiments, the provided methods and apparatuses may be useful in identifying and quantifying impurities as densities of from about 0.5-0.6 ppt, 0.6-0.7 ppt, 0.7-0.8 ppt, 0.8-0.9 ppt, 0.9-1.0 ppt, 1.0-1.1 ppt, 1.1-1.2 ppt, 1.2-1.3 ppt, 1.3-1.4 ppt, 1.4-1.5 ppt, and combinations thereof. In some embodiments, the provided methods and apparatuses provide a substantial improvement over conventional methods and apparatuses.

According to various embodiments, provided is a photoluminescence spectroscopy system for identifying and quantifying impurities in a semiconductor sample, comprising: (i) a laser system adapted to provide a defocused collimated laser beam capable of causing an illuminated semiconductor to photoluminesce, (ii) one or more semiconductor samples, each comprising a first surface adapted to be at least partially illuminated by the defocused laser beam, a substantially orthogonal second surface, and an edge at the intersection of the first and second surfaces adapted to allow collection of photoluminescence emitted therefrom, and (iii) a collection lens having a lens focal point at the edge of a sample positioned for analysis, the lens adapted to collect emitted photoluminescence at said focal point. The provided system is configured such that when a sample is positioned for analysis, its first surface is oriented to be at an angle of deviation of from about 0° to 90° with respect to a position parallel to the collection lens.

In some embodiments, the provided spectroscopy system comprises a laser defocusing system comprising a first lens that collects and focuses a collimated input laser beam to a laser focal point within the defocusing system, and a second lens that collects and magnifies the focused laser beam at the laser focal point to form as an output, the defocused collimated laser beam.

In some embodiments, the provided spectroscopy system comprises a rotatable sample holder comprising two or more projections radially configured around a central post, each projection adapted to hold a semiconductor sample, the projections alternately rotatable into position for analysis. In some embodiments, an electric motor is in communication with the holder central post, the motor capable of causing rotation of the holder.

In some embodiments, the provided system comprises a computer in communication with the electric motor, the holder, and the laser system, the computer programmed to (i) direct the electric motor to rotate the holder such that a sample on a projection holder is positioned for analysis, (ii) direct the laser system to illuminate at least a portion of the first surface of the sample positioned for analysis with the defocused laser beam, (iii) direct collection of emitted photoluminescence from the second surface of the sample positioned for analysis, (iv) direct the electric motor to rotate the holder such that a sample on another projection is positioned for analysis, and (v) repeat steps (ii)-(iv) until all samples have been analyzed.

Edge-On Collection of Photoluminescence

Figure 1:
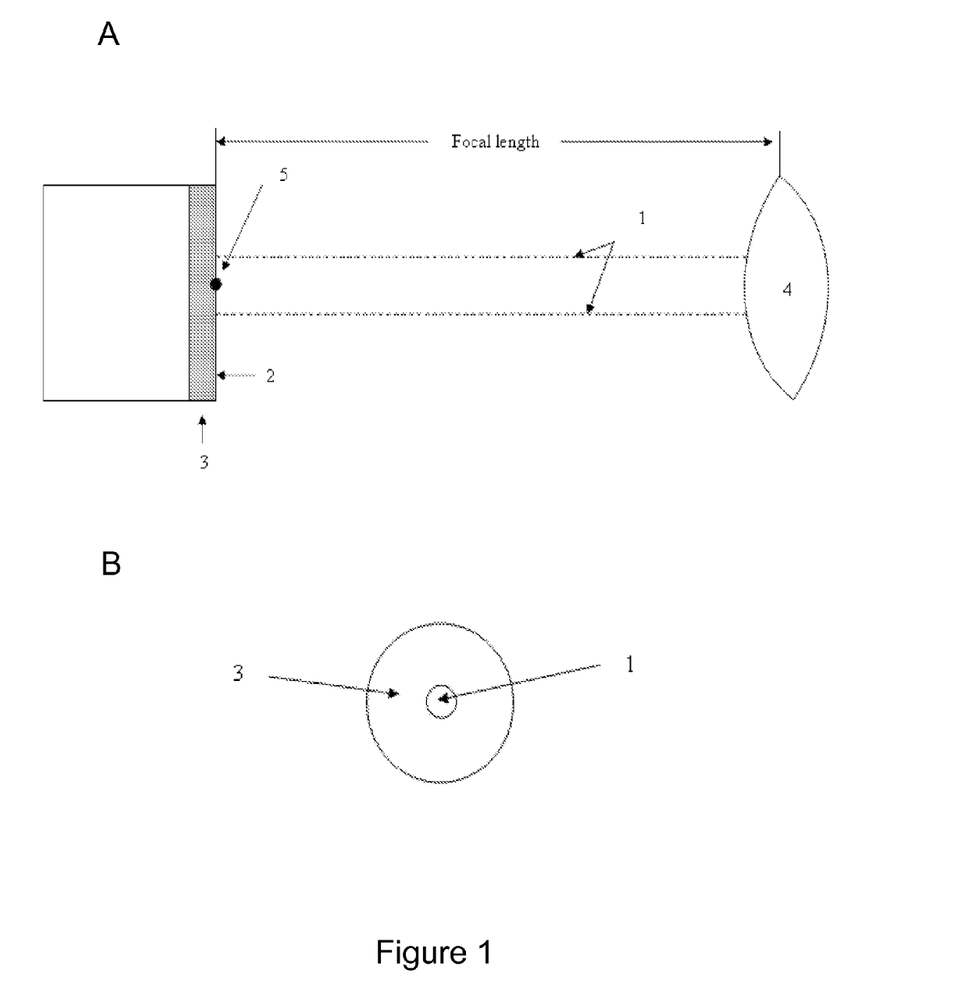
FIG. 1 illustrates one example of a conventional photoluminescence spectroscopy system involving "straight-on" collection of emitted photons from a semiconductor sample, wherein A depicts a schematic side view of a conventional system, and B depicts a front view of a sample being illuminated by a laser beam within said conventional system.

In some embodiments, the provided systems and methods involve "edge-on" collection of photoluminescence from a sample, which differs from the conventional technique used in the silicon industry. The conventional methods and instrumentation used in industry for collecting emitted photons from semiconductor samples involves a "straight-on" technique wherein the front face of a sample (i.e., the surface illuminated by an excitation laser) is oriented at a position that is parallel to the collection optics. One example of a conventional "straight-on" system is illustrated in FIG. 1, wherein a collimated laser beam 1 illuminates the front face 2 of a semiconductor sample 3. As shown, area illuminated by the beam is approximately 20% of the front face 2. The front face 2 of the sample 3 is configured to be parallel to the photoluminescence signal collection optics 4, and the focal point 5 of the collection optics 4 is on the front face 2 of the sample 3. The distance between the front face 2 of the sample 3 and the collection optics 4 is the same as the focal length (not labeled) of the collection optics 4.

When a semiconductor sample is illuminated by a laser, electrons in the illuminated portion of the semiconductor surface are excited by the incident laser energy. Because the profile of the excitation power of the beam has a Gaussian distribution (i.e., bell-shaped curve), luminescence generated in the semiconductor comes from regions of differing excitation power densities over the beam area. Thus, when the "straight-on" technique is employed, the luminescence collected from the front face 2 of the sample 3 represents an average of photoluminescence across the spot size (i.e., high power) of the Gaussian-distributed excitation beam 1 and has a high density of excitation but does not represent homogeneous excitation over the entire semiconductor sample. Among other things, this heterogeneous excitation of the semiconductor sample, a feature typical of the "straight-on" technique, confounds photoluminescence spectra and has been shown to hinder sensitivity for detection and quantification of impurities in the sample. For example, while sensitivity may be influenced by factors such as instrument type and scanning time, detection of impurities below 10 ppt is typically not achievable using conventional techniques.

In contrast to the standard method, embodiments of the present invention utilize an "edge-on" technique in which the front surface of the semiconductor sample is positioned to be non-parallel to the collection optics, said position being a suitable angle of deviation away from the parallel position to allow for collection of photoluminescence from the edge of the sample.

In some embodiments, the angle of deviation is chosen to provide the highest degree of detection of photoluminescence from the edge of the sample. In some embodiments, a suitable angle of deviation of the front surface of the sample may be from about 0° to about 90° with respect to a position parallel to the optics. Accordingly, it is contemplated that the angle of deviation may be from 0°-5°, 5°-10°, 10°-15°, 15°-20°, 20°-25°, 25°-30°, 30°-35°, 35°-40°, 40°-45°, 45°-50°, 50°-55°, 55°-60°, 60°-65°, 65°-70°, 70°-75°, 75°-80°, 80°-85°, 85°-90°, and combinations thereof. In such orientation, the emitted photons collected come from the edge of the sample and the observed luminescence represents an average over the entire exciton density profile (in contrast to the "straight-on" technique) since all paths from the excited portion of the semiconductor to the emitting edge are similar. Thus, when the "edge-on" technique is employed, the luminescence observed has a lower density of excitation, as compared to the "straight-on" technique. Among other things, this has been shown to increase sensitivity for detection and quantification of impurities in the sample. Good results have been obtained with an angle of deviation of 45°. For angles between 0°-45° and 45°-90° photoluminescence data collected may represent a combination of emissions from the front surface (straight-on effect) and the sample edge (edge effect). The greater the angle of deviation away from 45°, the lower the signal response when photoluminescence is only collected from the sample edge. The above notwithstanding, selection of the desired angle of deviation may be based, at least in part, on the shape of samples being tested. For example, when samples are flat with rectangular or circular surface areas and have a defined thickness, an angle of deviation of 45° may provide the desired signal response when said samples are positioned by the provided sample holder. One of skill in the art will recognize that when samples have a different shape, or when different sample holders are used, an angle of deviation other than 45° may provide the desired signal response.

In contrast to the conventional technique, sensitivity below 2.0 ppt is achievable with an "edge-on" technique. For example, detection of impurities at densities as low as from about 1.0 to about 2.0 ppt may be achieved with the methods and apparatuses described herein when an "edge-on" technique is used.

In addition to greater sensitivity, because the curved surface at the sample edge allows more luminescence to escape from the semiconductor sample, as compared to a front face of the sample, more luminescence is observed when the methods and apparatuses described herein are used. Thus, a greater signal to noise ratio in resultant spectra may be achieved with the provided methods and apparatuses, as compared to spectra obtained from the "straight-on" technique. In some embodiments, greater sensitivity may be achieved by combining the "edge-on" technique with a laser defocusing technique.

Figure 2:
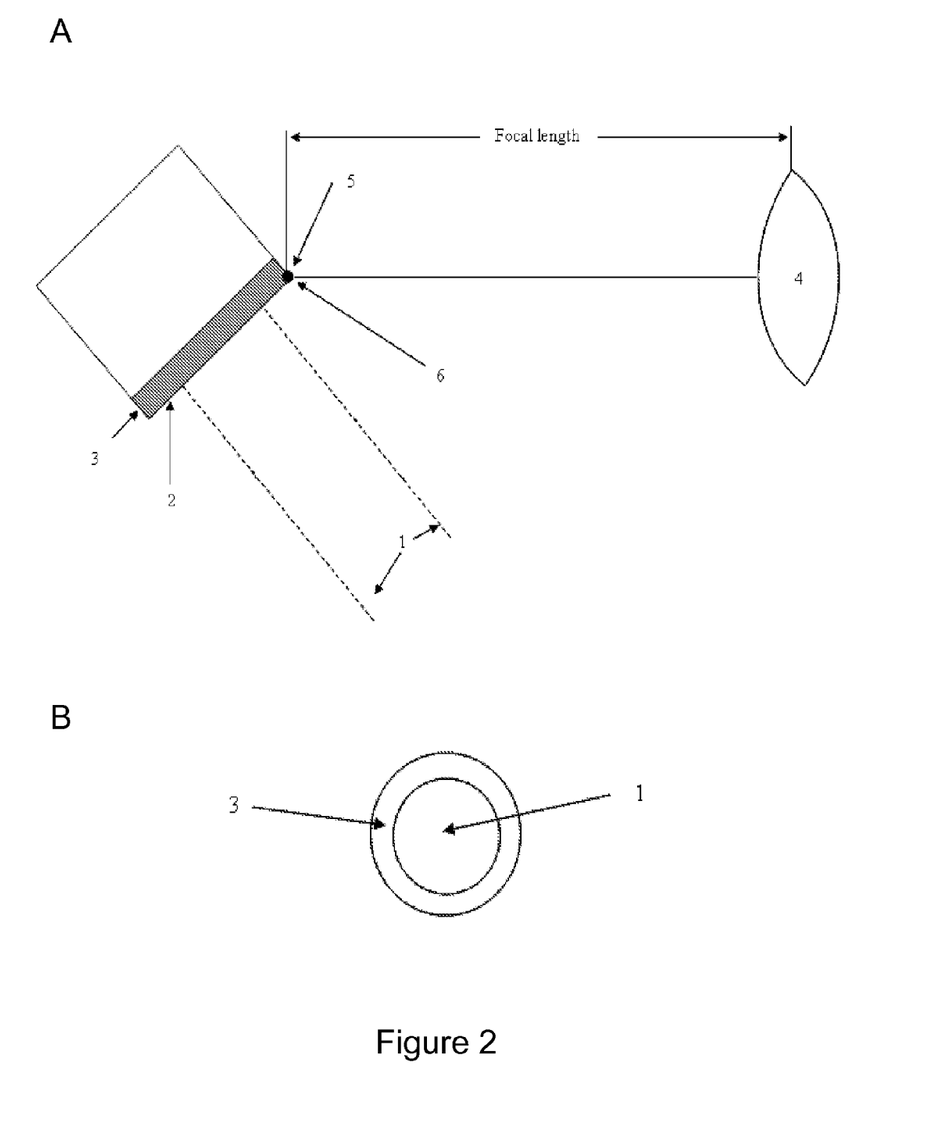
FIG. 2 illustrates one example of a provided photoluminescence spectroscopy system involving excitation of a semiconductor sample using a defocused laser and "edge-on" collection of emitted photons, wherein A depicts a schematic side view of a provided system, and B depicts a front view of a sample being illuminated by a laser beam within said provided system.

Referring to FIG. 2, illustrated is one example of a provided photoluminescence spectroscopy system wherein in some embodiments, light 1 from a light source (not labeled) is directed to the front face 2 of a semiconductor sample 3. The light source may be a laser, diode, or other light-emitting device suitable for generating electron-hole pairs in the sample. As illustrated, light 1 covers approximately 50-70% of the surface area of the front face 2, but other degrees of surface area coverage are also contemplated. For example, it is contemplated that the beam may illuminate 50-100% of the surface area of the front face 2. In some embodiments, it is desirable to cover as much of the test sample surface area as is practical because illuminating a wider surface area excites a broader volume of the semiconductor material and results in impurity data that is representative of the entire test sample. Regardless of the degree of surface area coverage desired, the provided methods and apparatuses involve positioning the front face 2 of the sample 3 to be non-parallel to the collection optics 4, said position being a suitable angle of deviation away from the parallel position associated with the "straight-on" technique. For example, the angle of deviation of the front face 2 may be from about 0° to about 90° with respect to a position parallel to the collection optics. Regardless of the specific angle of deviation chosen, the focal point 5 of the collection optics 4 is on the edge 6 of the sample 3 rather than the front face 2. In some embodiments, the front face 2, edge 6, or both are polished. In some embodiments, the front face 2, edge 6, or both are etched. The depicted system is configured for "edge-on" collection of emitted photons. The photoluminescence gathered with the collection optics 4 may be guided through a spectrometer (dispersive or fourier-transform) designed to collect spectroscopic data between 1050 to 1150 nm, and detected by a suitable detecting system (not shown), such as a CCD array, solid state detector, photodiode, or any other suitable detecting system or device, and the spectra are processed to generate data corresponding to impurities located in the sample. The generated data may comprise sample impurity identity, sample impurity quantity, or both. Processing of the detected photoluminescence may be by a microprocessor or similar device and may include a software program to perform spectral subtractions, spectral deconvolutions, or measurement of spectral peak areas as needed using any available software tools to process the spectra. Examples of available software tools include, but are not limited to, GRAMS Spectroscopy Software (Galactic Industries Corporation). Processors, programs, or both may be included in or associated with the detector and/or with other elements of the photoluminescence spectroscopy system or may be separate from other elements of the system. The photoluminescence spectroscopy system may further comprise any additional or alternative components for performing photoluminescence spectroscopy on a sample. For example, the system may include a display screen for visually displaying photoluminescence data, a sample holder for supporting the sample, one or more filters for filtering incident or return light, as well as any other suitable components. In some embodiments, the spectroscopy system comprises a system for defocussing the laser beam diameter prior to sample illumination, which allows for resolution of the BE and FE peaks with respect to the EHD peak without the need to vary or reduce incident laser power.

Good results have been obtained with the use of dispersive or Fourier Transform PL (FTPL) spectrometers and liquid nitrogen collected IR detectors. Good results have been obtained with dispersive spectrometers such as THR 1000 (Jobin-Yvon) and SPEX 1000M (Jobin-Yvon). Good results have also been obtained with FTPL spectrometers such as a Vertex 80V (Bruker Optics, Inc.). In some embodiments, when selecting a dispersive spectrometer for use with the provided methods and apparatuses, the aperture value should be low, such as from f/7.5 to f/8. In some embodiments, when selecting a FTPL for use with the provided methods and apparatuses, resolution and scanning frequency should be considered. For example, good results have been obtained with a resolution of 0.2 cm-1 and scanning frequency of 110 spectra/second.

In some embodiments, when selecting an IR detector, responsivity (a measure of conversion of optical to electrical energy) and NEP (a measurement of noise in the detector chip) should be considered. Good results have been obtained with detectors comprising Indium-Gallium-Arsenide (In-GaAs) photodiodes (e.g., Electro-Optical Systems) that have responsivity around $0.7 \times 10^{10}$ V/W within the region of interest (1050-1150 nm) and NEP of $4 \times 10^{-15}$ W/Hz$^{1/2}$.

In some embodiments, when a dispersive spectrometer is used, the detector data is sent to a lock-in-amplifier so that the detector signal may be sequenced with the chopper frequency that pulses the incoming laser beam at a 10-15 Hz cycle. Good results have been obtained with a SR810 amplifier (Stanford Research). The lock-in-amplifier transmits the data to a computer through any one of a variety of communication cards. Spectrometer control, data acquisition, instrument calibration, and data processing may be accomplished using a software system, such as one permitting data scripting using Array Basic programming. Good results have been obtained using GRAMS Spectroscopy software. In some embodiments, when a FTPL spectrometer is used, the detector data is transmitted into a software package (e.g., OPUS/IR) that can also operate the acquisition and control of the spectrometer. A scripting program, such as one using Array Basic, may also be used for data handling, instrument calibration, and data processing of the spectra.

Although not used in industry for detection and quantification of impurities in a sample, collection of photoluminescence at 45° from the edge of a silicon sample is known to be useful in the preparation of impurity calibration charts, as is described in Colley et al., "Calibration of the photoluminescence technique for measuring B, P and Al concentrations in Si in the range $10^{12}$ to $10^{15}$ cm$^{-3}$ using Fourier transform spectroscopy," *Semicond. Sci. Technol.* 2 (1987) 157-166. It is not known, however, to collect photoluminescence from the edge of a semiconductor sample for the purpose of detecting and quantifying impurities in the sample, wherein the sample is excited with a defocused incident laser beam.

Defocused Laser Excitation of Sample

In some embodiments, the provided photoluminescence spectroscopy systems and methods involve using a defocused laser beam to illuminate and excite a semiconductor sample. This is in contrast to conventional photoluminescence spectroscopy used in the silicon industry, which involves a focused laser beam being directed onto a portion of the front face of a silicon sample. For example, 25% of the front face may be illuminated with the laser beam. With a dispersive infrared spectrophotometer, high incident laser power is used, and with a Fourier transform instrument, lower incident laser power is used. However, spectra resulting from both instrument types suffer from interference between the BE, FE, and EHD peaks. Known methods of overcoming such difficulties typically involve varying the sample excitation energy.

Various embodiments of the present invention allow for enhanced resolution of the BE peak with respect to the EHD peak by using a defocused laser beam for illumination of at least a portion of the front face of the semiconductor sample. In some embodiments, the defocused laser beam excites from about 50-100% of the front face of the sample. Accordingly, it is contemplated that the illuminated surface area of the front face of the sample may be from about 50-55%, 55-60%, 60-65%, 65-70%, 70-75%, 75-80%, 80-85%, 85-90%, 90-95%, 95-100%, and combinations thereof.

Use of a defocused laser allows for reduced excitation energy without the need to reduce incident laser power, and at lowered excitation energy, the BE peak tends to be more prominent in spectra than the EHD peak. More accurate measurement of the BE and FE peaks in the TO-phonon region is achievable since an increase in signal-to-noise ratio occurs with the reduction of the EHD peak strength, and the defocused laser beam permits operating at higher incident laser power relative to a non-defocused laser beam. In addition, using a lowered excitation density enhances calibration accuracy and consistency between different photoluminescence instruments since calibrations using logarithmic ratios of the BE peak to a reference FE peak become non-linear at high excitation densities where the EHD peak becomes evident.

Use of a defocused laser in various embodiments of the instant invention differs from known use of defocused lasers. One example of a known use of a defocused laser is to increase illumination area on silicon wafers as part of laser tuning techniques, as described in Trupke et al., "Very efficient light emission from bulk crystalline silicon," *Appl. Phys. Letter*, 82, no. 18, 2997 (5 May 2003). Trupke et al. describe a laser tuning technique that involves increasing silicon free exciton emission off the front-face surface by increasing laser illumination area, wherein increased illumination area is achieved by defocusing the laser. Unlike the technique of Trupke, the methods and apparatuses provided herein increase impurity bound-exciton emissions relative to the free exciton emissions, and simultaneously decrease interferences from the electron hole droplet emissions while maintaining a fixed laser power. Thus, use of a defocused laser in embodiments of the instant invention involves increasing efficiency of impurity band emissions (phonon-assisted and non-phonon) and is indifferent to behavior of free exciton emissions. This is supported by the observance that FE peaks in spectra obtained with the instant techniques show little change with respect to spectra obtained using conventional techniques. Moreover, nowhere in Trupke is there any teaching or suggestion of a defocused laser used in combination with an "edge-on" collection technique for identifying and quantifying impurities in a sample.

Figure 3:
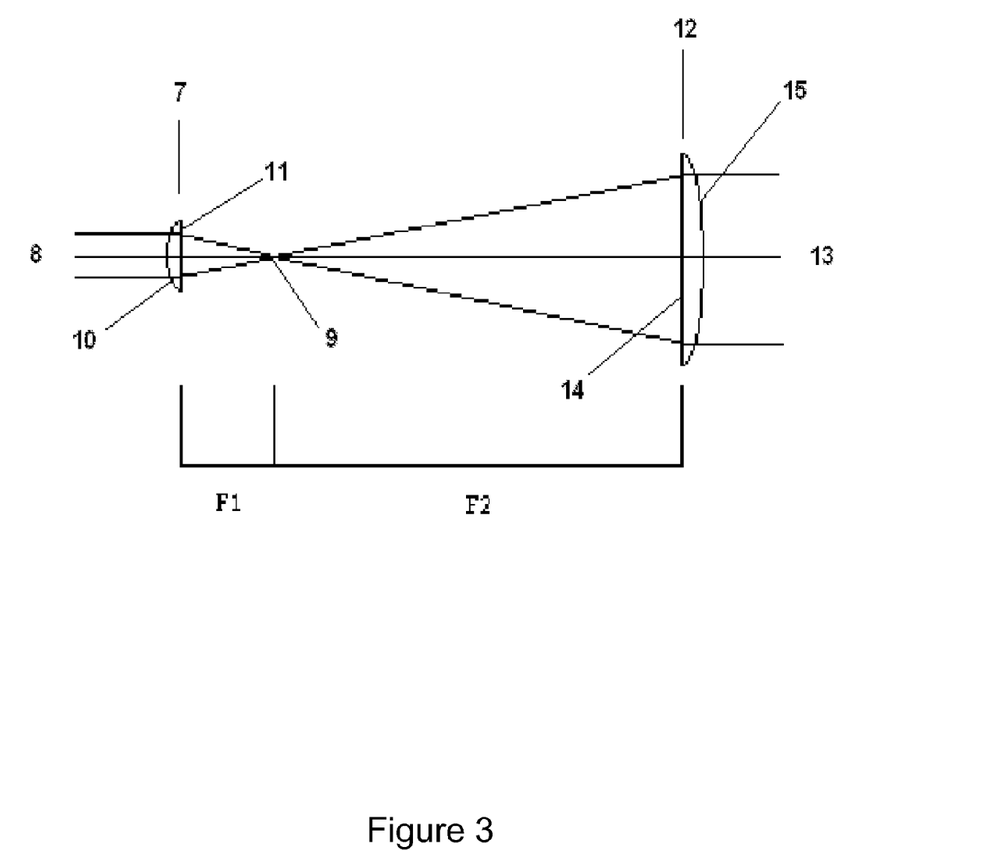
FIG. 3 illustrates schematically one example of a provided optical system for defocusing a laser beam, wherein F1 and F2 refer to the focal lengths of the respective lenses.

In some embodiments of the instant methods and apparatuses, a defocused laser is used in combination with "edge-on" collection of emitted photoluminescence. In some embodiments, a defocused laser may also be used in combination with "straight-on" collection of emitted photoluminescence. Regardless of the collection technique used, defocusing of the laser beam may be, but is not required to be, achieved with an optical defocusing system comprising a first lens having a first variable focal length and a second lens having a second variable focal length, wherein the first focal length is less than the second focal length. One example of such an optical system is illustrated in FIG. 3. As shown, the system comprises a first lens 7 that collects and focuses a collimated input laser beam 8 from a laser to a focal point 9, said focal point 9 being a variable length (F1) from the first lens 7. In some embodiments, the first lens 7 is a plano-convex lens having a substantially convex side 10 oriented toward the input laser beam 8 and a substantially planar side 11 opposite thereto and oriented toward the focal point 9. The system also comprises a second lens 12 that collects and magnifies the focused laser beam at the focal point 9 to form a collimated defocused output beam 13, said second lens 12 being a variable length (F2) from the focal point 9. In some embodiments, the second lens 12 is a plano-convex lens having a substantially planar side 14 oriented toward the focal point and a substantially convex side 15 opposite thereto and oriented toward the sample (not shown). The defocused output beam 13, which is used to illuminate a semiconductor sample, has a wider diameter and reduced intensity per given area as compared to the input beam 8.

Sample Holder

In various embodiments, the provided systems and methods involve collection of photoluminescence from the edge of a semiconductor sample, wherein the sample is held in a position for analysis by a provided sample holder that differs from conventional holders used in photoluminescence analysis.

Conventional photoluminescence spectroscopy in the silicon industry involves focusing a laser beam onto the front face of a silicon sample held in a cryostat, wherein the sample is oriented parallel to a cryostat window through which the laser beam shines and through which the photoluminescence is collected by collection optics that are parallel to the sample. In contrast, some embodiments of the present invention utilize a multi-sample holder that is adapted to allow an edge of the sample to be located proximate to a cryostat window through which edge luminescence may be collected by collection optics. The sample holder also orients the front surface of the sample under analysis so that it may be illuminated by a laser beam, said orientation being from about 0° to about 90° with respect to a position parallel to the collection optics. In some embodiments, the provided holder is adapted to hold samples without substantial strain or other stress on or to the sample. In some embodiments, the provided holder may be immersed in liquid helium or other suitable cryogenic liquid held within the cryostat. In some embodiments, the provided holder may be held within a cryostat that is cooled by a closed-cycle refrigeration system.

Figure 4:
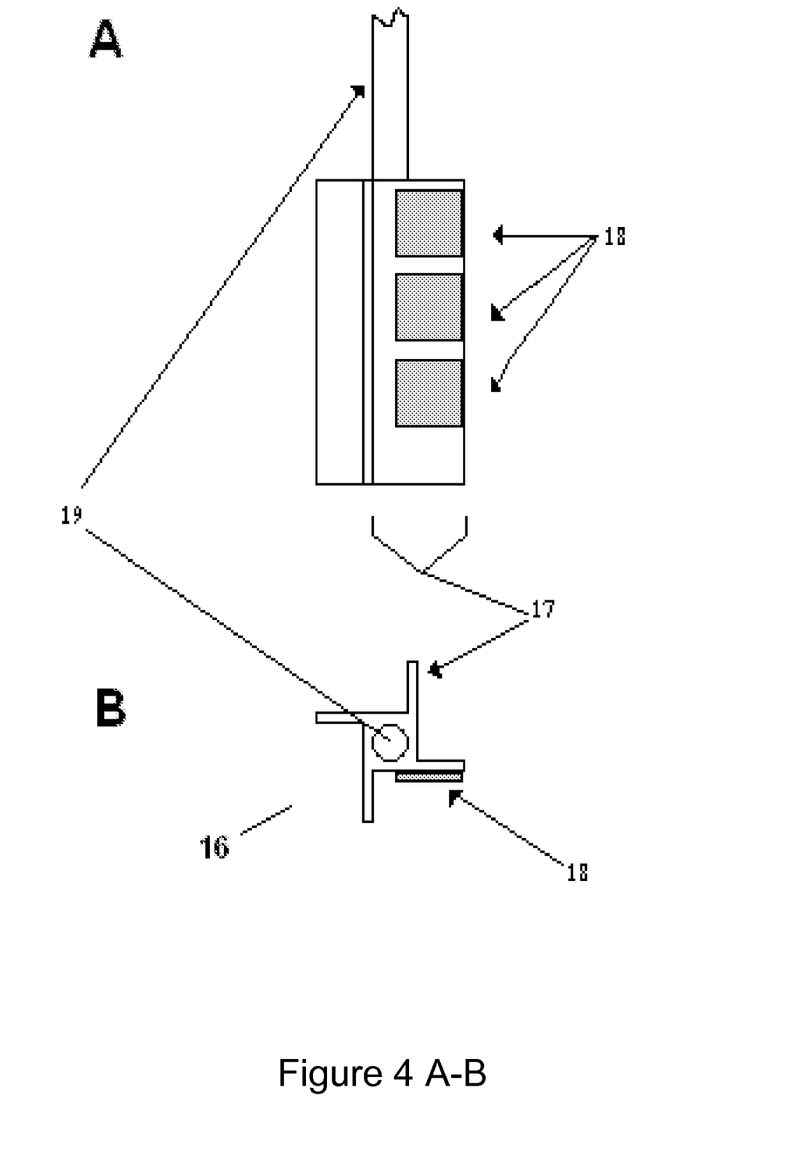
FIG. 4 illustrates schematically one example of a provided sample holder for use in a provided spectroscopy system, wherein A depicts a side view of one portion of the holder, B depicts a top view of the holder, C depicts a side view of one portion of the holder immersed within a cryostat, and D depicts a top view of the holder immersed within a cryostat.

One example of a provided holder is illustrated in FIG. 4. As shown, the holder 16 comprises four projections 17, each capable of holding at least one sample 18. It is, however, contemplated that a holder 16 could have fewer or more than four projections 17, that each projection 17 could be capable of holding more than one sample 18, or combinations thereof. For example, it is contemplated that a holder could comprise two or more projections, each projection may hold from 1 to 5 samples, that the samples on a projection may be arranged in a vertical manner, or combinations thereof. The projections 17 of the holder 16 are radially configured around a rotatable central post 19, wherein rotation of the central post 19 causes the sample 18 on a projection 17 to rotate to or from a position at which photoluminescence analysis occurs (i.e., the position at which a sample is illuminated by the laser beam and resulting luminescence is collected from the sample edge). Rotation of the holder 16 may be achieved manually or by an electric motor. Regardless of method of rotation, when a projection 17 of a holder 16 is properly positioned for analysis, the front surface (not labeled) of the sample 18 is open to illumination by the laser beam (not shown) and the edge (not labeled) of the sample 18 is proximate to a window 20 of a cryostat (e.g., cryostat from Janis Research Company) such that edge luminescence may be collected through the window 20 by the collection optics 21. In some embodiments, the holder 16 may be moved in a horizontal plane, a vertical plane, or combinations thereof.

In some embodiments, the provided holder may be manually rotated, moved horizontally, moved vertically, or combinations thereof in order to properly position samples for analysis. In some embodiments, the provided holder may be mechanically rotated, moved horizontally, moved vertically, or combinations thereof through in order to properly position samples for analysis in an automated or semi-automated manner. The central post of the holder may be in mechanical communication with one or more electric motors, thereby allowing for mechanical communication between the motor and the projections of the holder. It is contemplated that any motor suitable for use with spectroscopy systems may be used, including but not limited to servo motors, brushless motors, brush-type motors, and stepper motors. In some embodiments, it is contemplated that movements of the holder may be achieved by an electric motor in communication with a microprocessor. In some embodiments, the microprocessor may be in communication with one or more of the electric motor, the laser, and the collection optics such that movement of the holder, illumination of the samples, and collection of edge photoluminescence is automated. For example, the holder may automatically be rotated at precise intervals (e.g., 105°) for analysis. In some embodiments, it is contemplated that a computer in communication with the electric motor, the holder, and the laser system may be programmed to (i) rotate a sample holder that such a sample contained on projection thereof is suitably positioned with respect to collection optics for analysis of edge photoluminescence, (ii) illuminate the front faces of a suitably positioned sample with the defocused laser, (iii) collect resulting edge photoluminescence from the edge of the sample, and (iv) rotate the sample holder such that a sample held on another projection of the holder is suitably positioned with respect to collection optics for analysis of edge photoluminescence, and (v) repeat steps (i)-(iv) until all samples desired to be analyzed have been analyzed. In some embodiments, the computer may also be in communication with the collection optics.

Methods

According to various embodiments, provided are methods for identifying and quantifying impurities in a semiconductor sample using one or more of the provided apparatuses. In some embodiments, such methods are capable of generating data corresponding to sample impurity identity, sample impurity quantity, or both from samples having impurity densities as low as from about 0.5 ppt to about 1.5 ppt. Thus, the provided methods and apparatuses allow for analysis of sample impurities at densities of from about 0.5-0.6 ppt, 0.6-0.7 ppt, 0.7-0.8 ppt, 0.8-0.9 ppt, 0.9-1.0 ppt, 1.0-1.1 ppt, 1.1-1.2 ppt, 1.2-1.3 ppt, 1.3-1.4 ppt, 1.4-1.5 ppt, and combinations thereof.

In various embodiments, the provided methods comprise: (i) directing a defocused collimated laser beam onto at least a portion of a first surface of a semiconductor sample positioned for analysis, the sample comprising a substantially orthogonal second surface, and an edge at the intersection of the first and second surfaces adapted to allow collection of photoluminescence emitted therefrom, (ii) generating collectable photoluminescence in the sample, (iii) collecting the photoluminescence from the edge of the sample using a collection lens, the lens adapted to collect emitted photoluminescence at a lens focal point on the edge, and (iv) generating data from the collected photoluminescence, the data corresponding to sample impurity identity, sample impurity quantity, or both. In practice of the provided methods, when the sample is positioned for analysis, its first surface is oriented to be at an angle of deviation of from about 0° to 90° with respect to a position parallel to the collection lens.

In some embodiments of the provided methods, the defocused collimated laser beam is formed by directing a collimated input laser beam through a first lens and a second lens, the first lens collecting and focusing the input laser beam to a laser focal point and the second lens collecting and magnifying the focused laser beam at the laser focal point to form the defocused beam. In some embodiments, the first lens is a plano-convex lens having a substantially convex side oriented toward the input laser beam and a substantially planar side oriented toward the laser focal point, and the second lens is a plano-convex lens having a substantially planar side oriented toward the laser focal point and a substantially convex side oriented toward a sample positioned for analysis.

In some embodiments of the provided methods, the sample is held by a projection of a rotatable sample holder, the holder comprising two or more projections radially configured around a central post, each projection adapted to hold a sample and alternately rotate into the position for analysis. In some embodiments, the holder central post is in mechanical communication with an electric motor capable of causing rotation of the holder.

In some embodiments, it is contemplated that the provided methods are implemented by a computer in communication with the electric motor, the holder, and a system for generating the defocused laser beam, the computer programmed to (i) direct the electric motor to rotate the holder such that a sample on a projection is positioned for analysis, (ii) direct the defocused collimated laser beam to illuminate at least a portion of the first surface of the sample positioned for analysis, (iii) direct collection of emitted photoluminescence from the second surface of the sample positioned for analysis, (iv) direct the electric motor to rotate the holder such that a sample on another projection is positioned for analysis, and (v) repeat steps (ii)-(iv) until all samples have been analyzed.

In some embodiments, the computer may be in communication with and programmed to direct a suitable system or devices, such as a CCD array, a spectrometer, or any other suitable detecting system or device, to detect the collected photoluminescence. The detected photoluminescence may be processed by a microprocessor or similar device to generate data corresponding to impurities located in the sample. Processing of the detected photoluminescence to generate data may be performed by a software program. The generated data may comprise sample impurity identity, sample impurity quantity, or both.

EXAMPLES

The present invention will be better understood by reference to the following examples which are offered by way of illustration and which one of skill in the art will recognize are not meant to be limiting.

Example 1

Single crystalline silicon sample slices of approximately 14 mm diameter and 1 mm thickness were immersed in liquid helium level and then exposed to 200 mW of 514.5 nm laser excitation (from a Lexel Argon Ion Laser) and data was collected on a dispersive photoluminescence instrument.

Spectra were collected using four different operating configurations. First, a collimated laser beam of about 2 mm diameter was shone onto the front surface of the sample and photoluminescence was collected using a lens mounted parallel to the sample slice surface with the sample surface positioned at the focal point of the collection lens. Second, a collimated laser beam of about 2 mm diameter was directed into an optical defocusing system comprising a first lens having a first variable focal length and a second lens having a second variable focal length, wherein the first focal length is less than the second focal length. The laser beam exiting the defocusing system had a diameter of about 7 mm and was shone onto the front surface of the sample and photoluminescence was collected using a lens mounted parallel to the sample slice surface with the sample surface positioned at the focal point of the collection lens. Third, a collimated laser beam of about 2 mm diameter was shone onto the front surface of the sample and photoluminescence was collected using a lens that was positioned to place the edge of the sample at the focal point of the collection lens. Finally, a collimated laser beam of about 2 mm diameter was directed into an optical defocusing system comprising a first lens having a first variable focal length and a second lens having a second variable focal length, wherein the first focal length is less than the second focal length. The laser beam exiting the defocusing system had a diameter of about 7 mm diameter and was shone onto the front surface of the sample. Photoluminescence was collected using a lens that was positioned to place the edge of the sample at the focal point of the collection lens. In all operating configurations, the photoluminescence collected through the collection lens was focused into a Jobin-Yvon THR 1000 Spectrometer using a 1200 gr/mm 120×140 mm diffraction grating for dispersion, then focused onto an Indium-Gallium-Arsenide photodiode detector (Electro-Optical Systems) for data collection. Spectral analysis was performed using GRAMS Spectroscopy Software (Galactic Industries Corporation).

Table 1 demonstrates the effects on peak absolute intensity at the intrinsic silicon vibration (1130.2 nm) and the transverse optical vibrations for boron (1134.7 nm) and phosphorus (1135.5 nm). For all samples and all impurities, the spectral response was measured in Millivolts at the sample peak height positions for the free exciton (1130.2 nm) line for silicon and the bound exciton lines for the transverse optical (TO) lines for the boron (1134.7 nm) and phosphorus (1135.5 nm) species. When using the edge-on technique, these intensities increased by about eleven orders of magnitude with respect to the straight-on technique.

TABLE 1

| | Sample 1 Intensity (in Milli Volts) | | | Sample 2 Intensity (in Milli Volts) | | |
| --- | --- | --- | --- | --- | --- | --- |
| | Intrinsic Silicon (1130.2 nm) | Boron (1134.7 nm) | Phosphorus (1135.5 nm) | Intrinsic Silicon (1130.2 nm) | Boron (1134.7 nm) | Phosphorus (1135.5 nm) |
| Straight no lens | 19.23 | 0.96 | 1.34 | 24.17 | 0.63 | 2.72 |
| Straight lens | 16.51 | 0.89 | 1.41 | 20.55 | 0.61 | 2.59 |
| Edge no lens | 175.96 | 10.37 | 15.64 | 257.60 | 5.99 | 33.42 |
| Edge lens | 167.82 | 10.65 | 15.95 | 254.34 | 6.37 | 41.39 |

Figure 5:
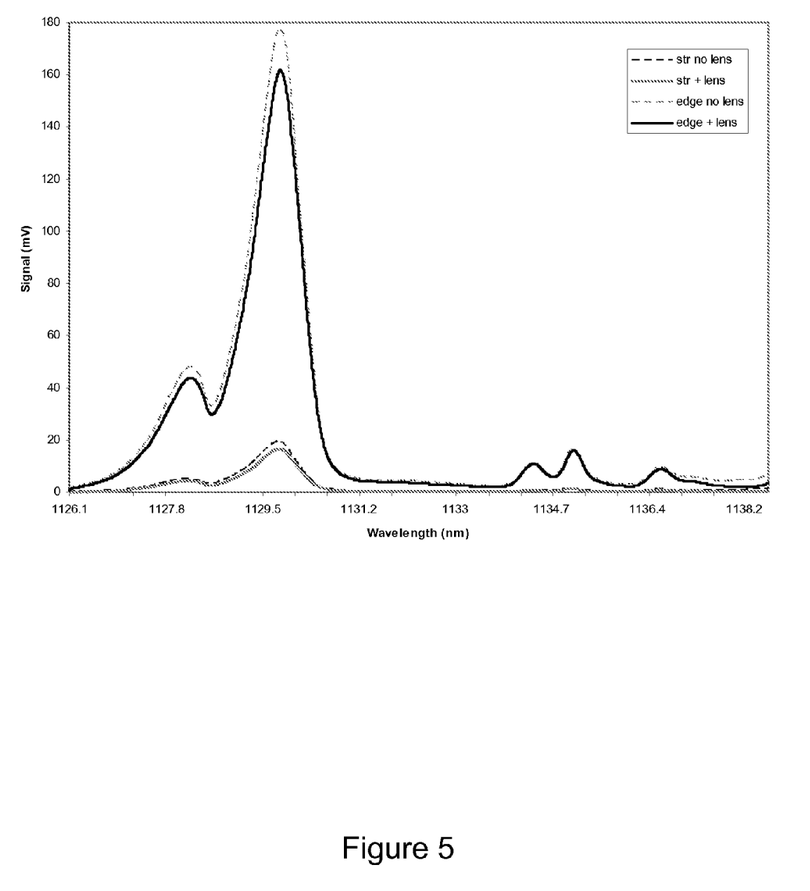
FIG. 5 is a photoluminescence spectrum demonstrating that edge-on photoluminescence provides greater peak intensity than straight-on photoluminescence.
Figure 6:
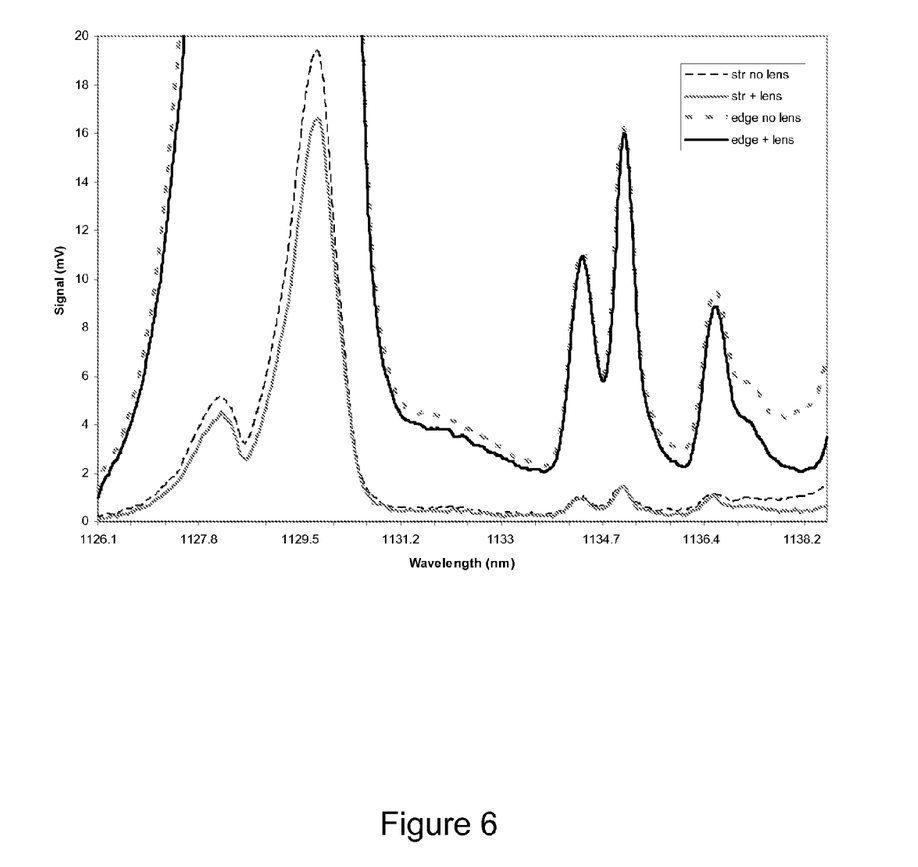
FIG. 6 is a photoluminescence spectrum demonstrating that use of a defocused laser beam decreases silicon intrinsic peak intensity when compared with a collimated laser beam technique, and has no correlating decrease in peak intensities for the bound exciton (BE) positions of impurities such as phosphorus and boron. Additionally, EHD effects are decreased when compared with the collimated laser beam technique.
Figure 7:
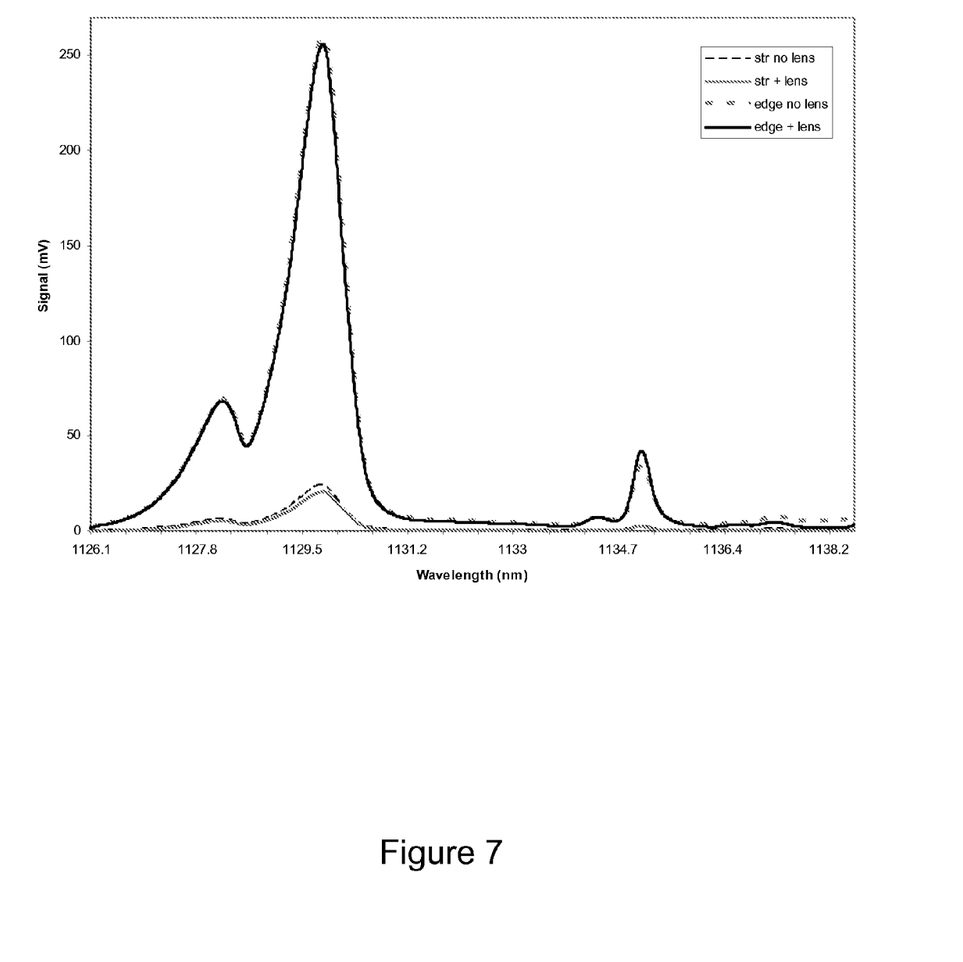
FIG. 7 is a photoluminescence spectrum demonstrating that edge-on photoluminescence provides greater peak intensity than straight-on photoluminescence.
Figure 8:
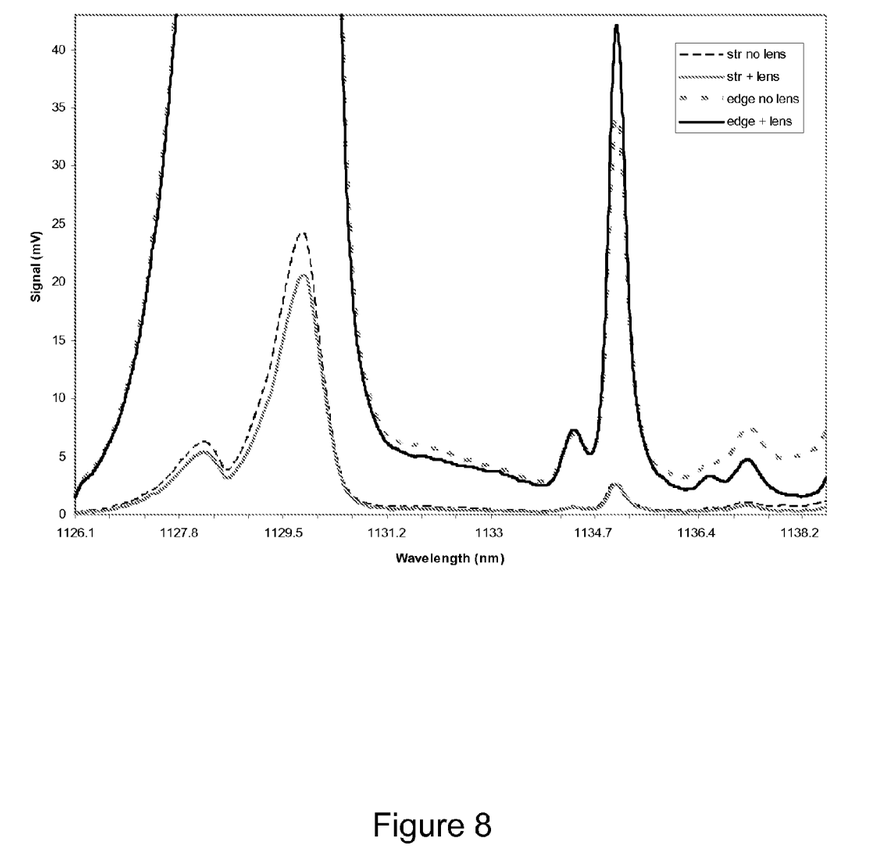
FIG. 8 is a photoluminescence spectrum demonstrating that use of a defocused laser beam decreases silicon intrinsic peak intensity when compared with a collimated laser beam technique, and has no correlating decrease in peak intensities for the bound exciton (BE) positions of impurities such as phosphorus and boron. Additionally, EHD effects are decreased when compared with the collimated laser beam technique.

FIGS. 5 and 7 demonstrate that, regardless of the laser beam diameter used, edge-on photoluminescence provides greater peak intensity than straight-on photoluminescence. Additionally, the use of a defocused laser beam on the sample surface showed enhanced spectral quality in the BE and EHD region (1130-1138 nm). For the samples that had their photoluminescence collected from the front surface (i.e., straight-on technique), defocusing the laser beam dropped the silicon intrinsic band (1130.2 nm) peak intensity by about 15%, although spreading the beam intensity over a larger section of the sample surface eliminated the electron-hole drop effects (FIGS. 6 and 8). For the samples that had their photoluminescence collected from the edge (i.e., edge-on technique), defocusing the laser also decreased the silicon intrinsic band intensity and eliminated the electron-hole drop effects. Additionally, the combination of an edge-on technique with a laser defocusing technique showed moderate increases in intensity for the boron (1134.7 nm) and phosphorus (1135.5 nm) lines.

The present invention should not be considered limited to the specific examples described herein, but rather should be understood to cover all aspects of the invention. Various modifications and equivalent processes, as well as numerous structures and devices, to which the present invention may be applicable will be readily apparent to those of skill in the art. Those skilled in the art will understand that various changes may be made without departing from the scope of the invention, which is not to be considered limited to what is described in the specification.

What is claimed is:

1. A photoluminescence spectroscopy system for identifying and quantifying impurities in one or more semiconductor samples, each comprising a first surface, a substantially orthogonal second surface, and an edge at the intersection of the first and second surfaces adapted to allow collection of photoluminescence emitted therefrom, the photoluminescence spectroscopy system comprising:
    a laser system adapted to provide a defocused laser beam capable of causing an illuminated semiconductor to photoluminesce; and
    a collection lens having a lens focal point at the edge of the one or more semiconductor samples positioned for analysis, the lens adapted to collect emitted photoluminescence from said focal point;
    wherein the system is configured such that when the one or more semiconductor samples is positioned for analysis, its first surface is oriented to be at an angle of deviation of greater than 0° and less than or equal to 90° with respect to a position parallel to the collection lens;
    wherein the first surface is adapted to be at least partially illuminated by the defocused laser beam;
    wherein the defocused laser beam is a defocused collimated laser beam; and
    wherein the laser system comprises a defocusing system comprising a first lens that collects and focuses a collimated input laser beam to a laser focal point within the defocusing system, and a second lens that collects and magnifies the focused laser beam at the laser focal point to form as an output, the defocused collimated laser beam.

2. The photoluminescence spectroscopy system according to claim 1, wherein the laser system is adapted to illuminate from about 50% to 100% of the first surface of a sample positioned for analysis.

3. The photoluminescence spectroscopy system according to claim 1, wherein the first lens is a plano-convex lens having a substantially convex side oriented toward the input laser beam and a substantially planar side oriented toward the laser focal point, and the second lens is a plano-convex lens having a substantially planar side oriented toward the laser focal point and a substantially convex side oriented toward a sample positioned for analysis.

4. The photoluminescence spectroscopy system according to claim 1, comprising a rotatable sample holder comprising two or more projections radially configured around a central post, each projection adapted to hold a semiconductor sample, the projections alternately rotatable into position for analysis.

5. The photoluminescence spectroscopy system according to claim 4, comprising
    an electric motor in communication with the holder central post, the motor capable of causing one or more of rotation, vertical movement, or horizontal movement of the holder.

6. The photoluminescence spectroscopy system according to claim 5, comprising a computer in communication with the electric motor, the holder, and the laser system, the computer programmed to (i) cause the electric motor to rotate the holder such that a sample on a projection is positioned for analysis, (ii) cause the laser system to illuminate at least a portion of the first surface of the sample positioned for analysis with the defocused laser beam, (iii) cause collection of emitted photoluminescence from the second surface of the sample positioned for analysis, (iv) cause the electric motor to rotate the holder such that a sample on another projection is positioned for analysis, and (v) repeat steps (ii)-(iv) until all samples have been analyzed.

7. The photoluminescence spectroscopy system according to claim 1 adapted to identify and quantify sample impurities at densities as low as from about 0.5 ppt to about 1.5 ppt.

8. The photoluminescence spectroscopy system according to claim 1, wherein the angle of deviation is about 45° with respect to the position parallel to the collection lens.

9. A photoluminescence spectroscopy method for identifying and quantifying impurities in a semiconductor sample, comprising:
    directing a defocused laser beam onto at least a portion of a substantially planar first surface of a semiconductor sample positioned for analysis, the sample comprising a substantially orthogonal second surface, and an edge at the intersection of the first and second surfaces adapted to allow collection of photoluminescence emitted therefrom;
    generating collectable photoluminescence in the sample;
    collecting the photoluminescence from the edge of the sample using a collection lens, the lens adapted to collect emitted photoluminescence from a lens focal point at the edge;
    generating data from the collected photoluminescence, the data corresponding to sample impurity identity, sample impurity quantity, or both; and
    directing a collimated input laser beam through a first lens and a second lens, the first lens collecting and focusing the input laser beam to a laser focal point and the second lens collecting and magnifying the focused laser beam at the laser focal point to form as an output, the defocused collimated laser beam;
    wherein when the sample is positioned for analysis, its first surface is oriented to be at an angle of deviation of greater than 0° and less than or equal to 90° with respect to a position parallel to the collection lens; and
    wherein the defocused laser beam is a defocused collimated laser beam.

10. The photoluminescence spectroscopy method according to claim 9 capable of generating the data from samples having impurity densities as low as from about 0.5 ppt to about 1.5 ppt.

11. The photoluminescence spectroscopy method according to claim 9, wherein the first lens is a plano-convex lens having a substantially convex side oriented toward the input laser beam and a substantially planar side oriented toward the laser focal point, and the second lens is a plano-convex lens having a substantially planar side oriented toward the laser focal point and a substantially convex side oriented toward a sample positioned for analysis.

12. A photoluminescence spectroscopy method for identifying and quantifying impurities in a semiconductor sample, comprising:
  directing a defocused laser beam onto at least a portion of a substantially planar first surface of a semiconductor sample positioned for analysis, the sample comprising a substantially orthogonal second surface, and an edge at the intersection of the first and second surfaces adapted to allow collection of photoluminescence emitted therefrom;
  generating collectable photoluminescence in the sample;
  collecting the photoluminescence from the edge of the sample using a collection lens, the lens adapted to collect emitted photoluminescence from a lens focal point at the edge; and
  generating data from the collected photoluminescence, the data corresponding to sample impurity identity, sample impurity quantity, or both;
  wherein when the sample is positioned for analysis, its first surface is oriented to be at an angle of deviation of greater than 0° and less than or equal to 90' with respect to a position parallel to the collection lens;
  wherein the defocused laser beam is directed onto from about 50% to 100% of the first surface of the sample positioned for analysis; and
  wherein the sample is held by a projection of a rotatable sample holder, the holder comprising two or more projections radially configured around a central post, each projection adapted to hold a sample and alternately rotate into the position for analysis.

13. The photoluminescence spectroscopy method according to claim 12, wherein the holder central post is in mechanical communication with an electric motor capable of causing one or more of rotation, vertical movement, or horizontal movement of the holder.

14. The photoluminescence spectroscopy method according to claim 13 implemented by a computer in communication with the electric motor, the holder, and a system for generating the defocused laser beam, the computer programmed to (i) direct the electric motor to rotate the holder such that a sample on a projection is positioned for analysis, (ii) direct the defocused collimated laser beam to illuminate at least a portion of the first surface of the sample positioned for analysis, (iii) direct collection of emitted photoluminescence from the edge of the sample positioned for analysis, (iv) direct the electric motor to rotate the holder such that a sample on another projection is positioned for analysis, and (v) repeat steps (ii)-(iv) until all samples have been analyzed.

15. The photoluminescence spectroscopy method according to claim 9, wherein the angle of deviation is about 45° with respect to the position parallel to the collection lens.

* * * * *